United States Patent [19]

Klesius et al.

[11] Patent Number: 4,505,277
[45] Date of Patent: Mar. 19, 1985

[54] IMPLANTATION DEVICE FOR USE IN VIVO STIMULATION AND COLLECTION OF MONOCYTES FROM PERITONEUM OF VERTEBRATE

[75] Inventors: Phillip H. Klesius, Auburn; Bobby G. Brown, Notasulga, both of Ala.

[73] Assignee: The United States of America as represented by the Secretary of Agriculture, Washington, D.C.

[21] Appl. No.: 407,232

[22] Filed: Aug. 11, 1982

[51] Int. Cl.³ ............................................. A61B 10/00
[52] U.S. Cl. .................................... 128/769; 128/1 R
[58] Field of Search ..................... 604/891, 19, 29, 48, 604/49, 85, 93, 183, 187, 264, 265, 317, 327, 328, 326; 128/769, 749, 750, 760, 1 R

[56] References Cited

U.S. PATENT DOCUMENTS 3,313,289 4/1967 Kapral ..................................... 3/1 X
4,364,394 12/1982 Wilkinson ........................... 604/392

OTHER PUBLICATIONS

Veale et al., "Differential Ability of Colonial Types of Neisseria Gonorroeae to Produce Infection and an Inflammatory Response in Subcutaneous Perforated Chambers in Guinea-Pigs and Rabbits", J. Med. Microbiol., vol. 8, 1975, pp. 325-334.

Primary Examiner—Stephen C. Pellegrino
Attorney, Agent, or Firm—M. Howard Silverstein; David G. McConnell; Raymond C. Von Bodungen

[57] ABSTRACT

An apparatus for in vivo stimulation and collection of monocytes from peritoneum of vertebrate is disclosed. The apparatus is implanted between the skin and the peritoneum. This device stimulates the production and growth of monocytes and at the same time attracts the monocytes into the apparatus. The apparatus comprises a container which has a plurality of membrane-covered holes for monocyte entry. There is an inlet and outlet conduit which is attached to opposing sides of the container to allow flushing. The conduits are equipped with a lock tip coupler for connection when the flushing operation is not taking place.

1 Claim, 1 Drawing Figure

IMPLANTATION DEVICE FOR USE IN VIVO STIMULATION AND COLLECTION OF MONOCYTES FROM PERITONEUM OF VERTEBRATE

BACKGROUND OF THE INVENTION

1. Field of the Invention

The instant invention relates to an apparatus for collecting monocytes from animals.

2. Description of the Prior Art

Yield of monocytes obtainable from peritoneal cavity of unstimulated animals is too low to make use of these monocytes. See Stuart, A. E., Habeshaw, J. A. and Davidson, A. E. in "Handbook of Experimental Immunology", p. 24.1 (Weir, Editor), Blackwell Scientific Publications, Osney Mead, Oxford, England, 1976. In man and other vertebrates, pulmonary monocytes can be obtained from unstimulated subjects by bronchopulmonary lavage. However, the procedure is considered to be relatively difficult, each monocyte collection requires separate isolation procedures, and the monocyte yields are relatively low. See Finley, T. N. and Ladman, A. J. New England Journal Medicine, 286, p. 223-227, 1972.

D. H. Burrin, et al., in British Experimental Pathology 47, 70-75, 1966 disclosed the isolation of monocytes from bovine blood by sedimentation techniques. The monocytes were found to be phagocytic for *Brucella abortus*. The purity and yield of monocytes were very poor because monocytes represent only 1% of the white blood cell population in the bovine Bovine monocytes were isolated from blood adherence to glass. However the yields of monocytes obtained by this method are poor, even with the use of large volumes of blood. See Fitzgeorge, R. P. et al., British Journal of Experimental Pathology 48, 522-528, 1967.

Mononuclear cells called monocytes have numerous biological functions are very important to immunity and defense.

The following references provide a ready review of pertinent information and data with respect to monocytes and their vital function in animals: *The Immunobiology of Macrophage*, 1976, compiled by Dr. D. S. Nelson, ed., Academic Press, N.Y.; *The Handbook of Experimental Immunology*, compiled by Dr. D. M. Weir, ed., 1976, Blackwell Scientific Publications, Oxford, England; *The Manual of Clinical Immunology*, compiled by Drs. N. R. Rose and H. Friedman, eds., 1976, and The American Society of Microbiology, Washington, D.C.

The yield of monocytes from the peritoneal cavity can be greatly increased by the use of inducing agents. The inducing agents are injected into the peritoneal cavity prior to harvesting monocyte exudate from the stimulated animal. The animal usually needs to be killed prior to monocyte harvesting, thereby limiting the kind of animal used. The best inducing agents are those that provoke an exudate rich in monocytes and that are biodegradable, leaving no trace in the cultured monocytes. The use of chemical inducing agents such as serum, glycogen, mineral oil, protease peptone broth, thioglycollate, casein, etc. have many drawbacks. See Stuart, A. E., Habeshaw, J. A., and Davidson, A. E. in "Handbook of Experimental Immunology", p. 24.2 (Weir, Editor), Blackwell Scientific Publications, Oxford, England, 1976.

Monocytes can be collected and purified from chickens by implantation of polysterene discs into the peritoneal cavity. The discs were removed after 4 days from the sacrificed chickens and transferred to petri dishes containing culture medium. The yield of monocytes was 3 to $4 \times 10^6$/chicken with a purity of 80%. The use of discs caused the stimulation of monocytes without the drawbacks of inducing agents. However, the yield and purity of monocytes were low. In addition, the animal must be killed prior to removal of the implanted discs and the harvest of monocytes. See Micalizio, S. and Della Bruna, C. Experimentia 5191,1109,1975.

Diffusion chambers of lucite rings with various membranes have been used to study monocytes without the use of inducing agents. The diffusion chambers were implanted into the peritoneal cavity of animals primarily to study the function of various cells rather than the collection of monocytes. Removal of the diffusion chambers from sacrificed animals was required to recover cell populations. See Shelton, E. and Rice, M. E. American J. Anatomy 105, 281, 341, 1959.

SUMMARY OF THE INVENTION

The apparatus is a simple device which is implanted between the abdominal wall and the peritoneum of an animal to be tested. The apparatus comprises a chamber with a plurality of holes in the outer surface. These holes are covered with an inert permeable membrane. Once implanted, the apparatus stimulates the production of monocytes in the animal. The monocytes migrate into the chamber through the permeable-membrane-covered holes where they gather and collect. The holes of this chamber, which are covered with inert permeable membrane, prevents external tissue from entering and growing within the container, but allows the migration and collection of individual cells (monocytes) within the chamber. The chamber is fitted with an inlet and outlet conduit on opposite sides of the chamber for continuous monocyte collection.

This invention represents a major improvement over the prior art. Heretofore, the collection of monocytes from peritoneum of veterbrate animals has always resulted in the sacrifice of the animal. This has severely limited the test data available for the study of this type of research. The preferred embodiment is an apparatus for in vivo stimulation of monocytes which results in a greater generation of monocytes from the peritoneum of the veterbrate. Furthermore, the monocytes are continuously collected from the peritoneum of veterbrates during the life cycle and no sacrificing of the life of the test subject is necessary. Therefore, the results obtained are not only more realistic but the statistical and anatomical studies are far superior to anything heretofore available.

DESCRIPTION OF THE PREFERRED EMBODIMENTS

Figure 1:
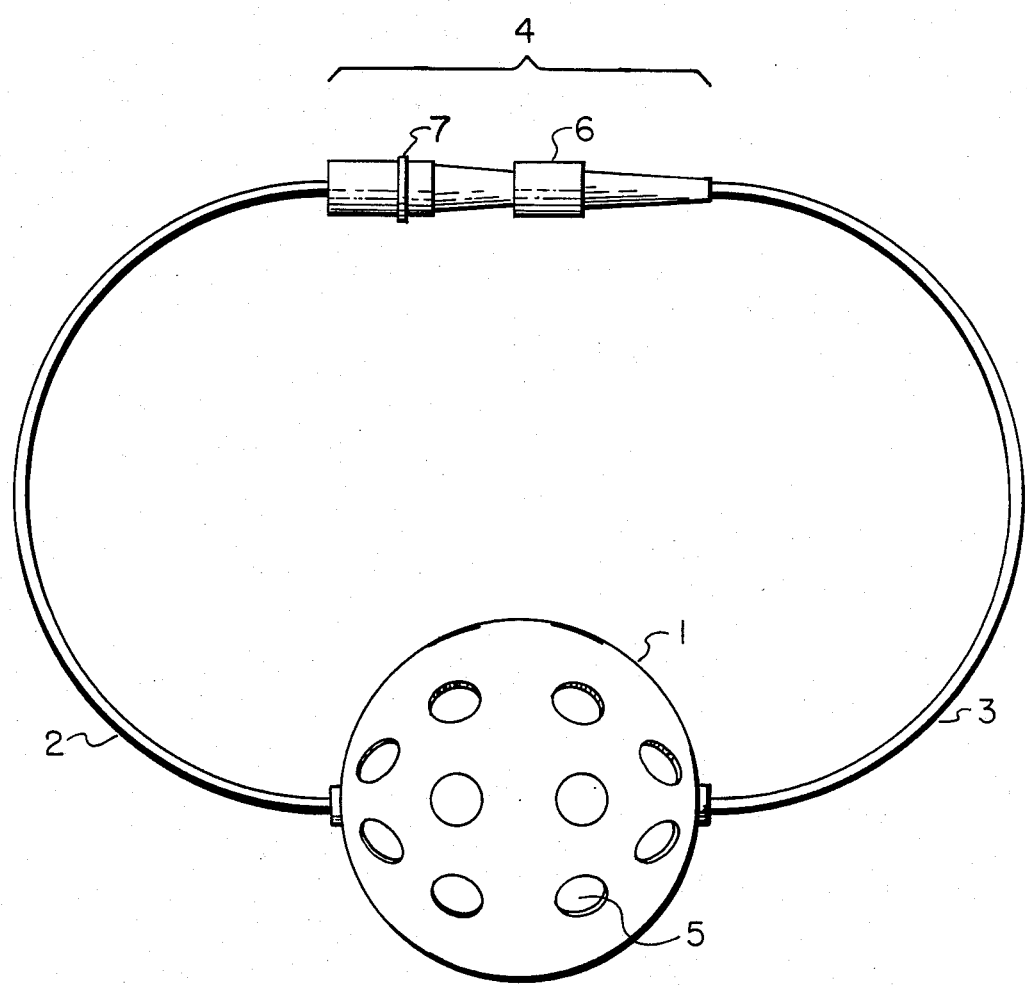
FIG. 1 is a front view of the apparatus showing all of the salient parts.

Referring now to the single FIG. 1 wherein a chamber 1, which is a sphere or a cylinder made of any material compatible with the implantation into a veterbrate, is fitted with a plurality of holes 5.

The holes are covered with a nylon or latex permeable membrane that selectively permits individual or single cell migration but excludes tissue ingrowth. Through one side of container 1 is affixed inlet conduit 2. Inlet conduit 2 extends into the hollow inside of chamber 1. Outlet conduit 3 is affixed through the opposing side of chamber 1. Outlet conduit 3 also extends into the inside of hollow chamber 1. The opposite ends of both inlet conduit 2 and outlet conduit 3 are fitted with complementary quick disconnect coupling 4 so that coupling 4 can be quick connected or disconnected at will. It should be noted that chamber 1 can take any configuration or size and this will be determined by the animal to be sampled. The entire apparatus is made to be disposable. Sterilization of the implantation device is possible by radiation or gas treatment following packaging in a suitable paper and/or cellulose-type wrapper. Conduits 2 and 3 form an external loop by passing through the skin. Male conduit coupling 5 serves as a vent for the implanted device during the irrigation and aspiration process. The imbedded device is held firmly implaced by a "walling off" process caused by initial reaction to the imbedded device. Larger veterbrates such as cattle would require the described device whereas smaller veterbrates could better use a one-half to one-fourth scale of the sphere or cylinder depending on the size and weight of the animal.

The monocytes have better than 95% viability and require usually only washing before culturing.

The monocytes collected are active phagocytically and are not contaminated with trace of inducing agents.

This implantation device is disposable and can be safely removed without endangering the animal's future use and health. Continuous collection of monocytes from the same animal even under different conditions is possible for long periods using the present invention.

The following example is provided to illustrate the process and product of this invention and should not be construed as limiting the invention in any manner whatever.

EXAMPLE

Animals and Surgical Preparation

Three holstein-friesian bull calves about 4 to 5 months of age weighing 90 to 100 kg were used. The calves were housed in individual pens under management practices devised to prevent disease.

The calves were prepared for surgical operation by withholding hay for 24 hours and grain and water for 12 to 18 hours. The hair of the right paralumbar fossa was removed (No 40 clipper blade) and the area was cleaned with water and providine iodine scrub.

The endotracheal tube was attached to a gas anesthetic machine where halothane was vaporized in 100% oxygen. The halothane concentration was started at 5% and reduced to 0.5 to 3% for maintenance during the remainder of the procedure.

The skin of the surgical site was prepared with providine solution. A skin incision, extending from the 5th lumbar veterbrae area to the last rib, was made ventral to the lumbar transverse processes. The incision was carried through the facia of orgin of the external abdominal oblique, internal abdominal oblique, and transverse abdominis muscles, just lateral to the epaxial muscles. This exposed the retroperitoneal spaces just caudal to the right kidney. By blunt dissection, the incision is deepened until the peritoneum is reached. The tissue overlying the peritoneum is bluntly separated beginning at the incision and extending 10 cm cranially.

IMPLANTATION DEVICE

In the case of the preferred embodiment, chamber 1 is a sphere made of white translucent, semi-flexible, nontoxic, nonpyrogenic, implantable and blood compatible polypropylene. Chamber 1 is a hollow sphere with a 1 21/32 OD inches and a 1 17/32 ID inches with wall thickness of 1/16 inch and is perforated with twenty four holes of 7/32 ID inch.

Plastic chamber 1 used in the procedure was fitted with conduit tubes 2 and 3 coupled by locktip adapters 4. These implantation devices were sterilized by ethylene oxide gas.

Plastic chamber 1 is pushed through the incision and along the dissection tract adjacent to the peritoneum to form a retroperitoneal pocket. The peritoneum is folded over the device so that plastic chamber 1 is surrounded by the peritoneum. Conduit tubes 2 and 3 in the chamber exited the body through a separate skin incision. Conduit tubes 2 and 3 were anchored to the skin by sutures. Once conduit tubes 2 and 3 were anchored in place, adaptors 4 are joined together so that an external loop is formed. The edges of the fascia of the abdominal muscles were apposed with sutures in a simple continuous pattern. The subcutaneous tissue was apposed likewise with sutures. The skin edges were brought in apposition with simple continuous sutures. The postoperative care consisted of a daily injection (IM) of procaine penicillin G for 5 days at dose rates 22,000 units/Kg. Conduit tube exit 3 was treated daily with Betadine Ointment to prevent infection.

Monocyte Collection Process

When large quantities of monocytes were needed, male end 5 of conduit 2 was fitted with sterile syringe for collection of monocytes. A syringe containing 30 ml of Hank's balanced salt solution (HBSS) with 5 units of heparin/ml was inserted into inlet conduit 2. The HBSS was gently pushed back and forth through conduit 2 into chamber 1 to irrigate the monocytes collected within this spherical holed chamber.

Irrigation means to flush out chamber 1 with the solution in the syringe (not shown) which is fitted to inlet conduit 2. Thus the asperates containing monocytes were collected from conduits 2 and 3 as well as chamber 1 by irrigation method. This irrigation is accomplished by disconnecting male adapter 5 from female adapter 6.

The aspirates collected from container 1 were centrifuged to produce monocyte pellets. ($100 \times g$ for 3.5 min). The supernatant was removed completely and the monocyte pellet was then resuspended by gentle agitation in tissue culture medium (TC 199 containing 10% heat inactivated fetal calf serum). The monocytes were washed once with 10 ml of TC 199. Erythrocyte contamination was removed if necessary by resuspending the cell pellet once in 2 ml sterile distilled water for 30 seconds and then rapidly adding 12 ml of $2 \times$ HBSS to restore isotonicity. The monocytes were counted in a standard hemocytometer after dilution with 3% acetic acid.

MONOCYTE ASSAYS

Viability of monocytes was done by the trypan blue exclusion test (See Tennant, J. R. Evaluation of trypan blue technique for determining of cell viability. Transplantation 2, 685 (1964). The ability of the monocytes to phagocytize was determined by incubating in the presence of latex particles. See Sabet, T. et al. A Simple Method for Obtaining Peritoneal Macrophages from chickens. J. Immunol. Methods 14, 103–110 (1977). In vitro assessment of monocyte migration was done by the agarose droplet technique described by Lavergne, J. A. and Harrington, J. T. In vitro Assessment of Delayed Hypersensitivity in the Human. Inhibition of Cell Migration from Agarose Microdroplets. J. Immunol. Methods 22, 111–121, (1978).

RESULTS AND DISCUSSION

The yield was 0.2 to $5 \times 10^7$ monocytes per implanted device/day. The monocytes can be collected from the device after it has been in place for 3 days and thereafter on a daily schedule as desired. The purity of monocytes was 90 to 97% and the viability was better than 95%. The majority of monocytes were phagocytically active (99.5 to 100%). Migration of the monocytes was good indicating the suitability for use in the Migration Inhibition Assay (MIF).

Collection of monocytes from the same calf was performed daily with yields averaging 0.2 to $5 \times 10^7$ monocytes/day. The device was functional for collecting monocytes over a period of at least 6 months. The majority of adherent monocytes collected are phagocytically active and have receptors for complement and FC portion of IgG, thus indicating the cells are macrophages.

We claim:

1. An apparatus for in vivo stimulation and collection of monocytes from peritoneum of vertebrate comprising in combination the following:
   (a) a spherical chamber to stimulate, receive and collect monocytes;
   (b) a plurality of nylon or latex permeable membrane-covered holes in said chamber to selectively permit individual or single cell migration of said monocytes into said chamber but to exclude tissue ingrowth;
   (c) a first conduit, one end of which is inserted through the side of said chamber to allow entry of fluid into said chamber;
   (d) a second conduit, one end of which is inserted through an opposing side of said chamber from said first conduit side, said second conduit to allow exit of fluid from said chamber;
   (e) a lock tip quick disconnect coupling device affixed to the ends of said first and second conduits which are not connected to said chamber, said coupling device to allow coupling of said first conduit to said second conduit and serve as a vent for the apparatus during an irrigation or aspiration process.

* * * * *